(12) United States Patent
Franks et al.

(10) Patent No.: US 8,088,736 B2
(45) Date of Patent: Jan. 3, 2012

(54) CTLA-4 PROTEIN VARIANTS

(75) Inventors: Ruth Franks, Granta Park (GB); Mark Terence Liddament, Granta Park (GB); Lutz Ulrich Jochen Wilhelm Jermutus, Granta Park (GB); Andrew Grier Buchanan, Granta Park (GB)

(73) Assignee: MedImmune Limited, Cambridge (GB)

( * ) Notice: Subject to any disclaimer, the term of this patent is extended or adjusted under 35 U.S.C. 154(b) by 83 days.

(21) Appl. No.: 12/446,216

(22) PCT Filed: Oct. 22, 2007

(86) PCT No.: PCT/GB2007/004023
§ 371 (c)(1),
(2), (4) Date: Apr. 17, 2009

(87) PCT Pub. No.: WO2008/047150
PCT Pub. Date: Apr. 24, 2008

(65) Prior Publication Data
US 2010/0322893 A1   Dec. 23, 2010

(30) Foreign Application Priority Data
Oct. 20, 2006   (GB) .................................. 0620934.0

(51) Int. Cl.
*A61K 38/17*   (2006.01)
*C07K 14/47*   (2006.01)
*C12P 21/04*   (2006.01)
*C12P 21/06*   (2006.01)
*G01N 33/53*   (2006.01)

(52) U.S. Cl. ...... 514/16.6; 514/21.2; 530/350; 530/402; 530/403; 435/69.1; 435/69.7; 435/7.1

(58) Field of Classification Search .................. None
See application file for complete search history.

(56) References Cited

U.S. PATENT DOCUMENTS
7,829,534 B2 * 11/2010 Larsen et al. .............. 424/134.1

FOREIGN PATENT DOCUMENTS
WO   WO 01/92337   12/2001
WO   WO 02/02638    1/2002
WO   WO 02/058729   8/2002

OTHER PUBLICATIONS

Carreno et al., "CTLA-4 (CD152) Can Inhibit T Cell Activation by Two Different Mechanisms Depending on Its Level of Cell Surface Expression," *Journal of Immunology*, vol. 165, pp. 1352-1356, 2000.
Foote and Winter, "Antibody Framework Residues Affecting the Conformation of the Hypervariable Loops," *J. Mol. Biol.*, vol. 224, pp. 487-499, 1992.
Larsen et al., "Rational Development of LEA29Y (belatacept), a High-Affinity Variant of CTLA4-Ig with Potent Immunosuppressive Properties," *American Journal of Transplantation*, vol. 5, pp. 443-453, 2005.
Morton et al., "Differential Effects of CTLA-4 Substitutions on the Binding of Human CD80 (B7-1) and CD86 (B7-2)," *Journal of Immunology*, vol. 156, pp. 1047-1054, 1996.

* cited by examiner

*Primary Examiner* — Marianne P Allen
(74) *Attorney, Agent, or Firm* — Klarquist Sparkman, LLP

(57) ABSTRACT

Protein variants of CTLA-4, which show increased activity compared to wild-type in a cell assay and which exhibit increased stability. Such variants are useful for treatment of disorders whereby attenuation of the T cell response would be beneficial.

19 Claims, 4 Drawing Sheets

| 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 |
|---|---|---|---|---|---|---|---|---|---|---|---|---|---|---|---|---|---|---|---|---|---|---|---|---|
| A | M | H | V | A | Q | P | A | V | . | V | L | A | S | S | R | G | S | A | S | F | V | C | E | Y |
|   |   | V |   |   |   |   |   |   |   |   |   |   |   |   |   |   |   |   |   |   |   |   |   |   |

| 26 | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 |
|---|---|---|---|---|---|---|---|---|---|---|---|---|---|---|---|---|---|---|---|---|---|---|---|---|
| A | . | P | P | S | K | . | . | . | A | T | E | V | R | V | T | V | L | R | Q | A | D | S | Q | V |
|   |   | V | V | V |   |   |   |   |   |   |   |   |   |   |   |   |   |   |   |   |   |   |   |   |

| 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 |
|---|---|---|---|---|---|---|---|---|---|---|---|---|---|---|---|---|---|---|---|---|---|---|---|---|
| T | E | V | C | A | A | T | Y | M | M | . | G | N | E | S | T | F | L | D | D | S | . | . | . | I |
|   |   | V | V | V |   |   |   |   |   |   |   |   |   |   |   |   |   |   |   |   |   |   |   |   |

| 76 | 77 | 78 | 79 | 80 | 81 | 82 | 83 | 84 | 85 | 86 | 87 | 88 | 89 | 90 | 91 | 92 | 93 | 94 | 95 | 96 | 97 | 98 | 99 | 100 |
|---|---|---|---|---|---|---|---|---|---|---|---|---|---|---|---|---|---|---|---|---|---|---|---|---|
| C | T | G | T | L | . | . | S | G | N | Q | V | N | L | T | I | Q | G | L | R | A | M | D | T | G |
| V |   | V |   | V |   |   | V |   |   |   | V |   |   |   |   |   |   |   |   |   |   |   |   |   |

| 101 | 102 | 103 | 104 | 105 | 106 | 107 | 108 | 109 | 110 | 111 | 112 | 113 | 114 | 115 | 116 | 117 | 118 | 119 | 120 | 121 | 122 | 123 | 124 | 125 |
|---|---|---|---|---|---|---|---|---|---|---|---|---|---|---|---|---|---|---|---|---|---|---|---|---|
| L | Y | I | C | E | V | E | L | M | Y | . | P | P | P | Y | Y | L | G | I | G | N | G | T | Q | I |
|   |   |   |   | V | V |   |   |   |   |   |   |   |   |   |   |   | V |   |   |   |   |   |   |   |

Figure 5

CTLA-4 PROTEIN VARIANTS

CROSS REFERENCE TO RELATED APPLICATIONS

This is the U.S. National Stage of International Application No. PCT/GB2007/004023, filed Oct. 22, 2007, which was published in English under PCT Article 21(2); which in turn claims the benefit of Great Britain Application No. 0620934.0, filed Oct. 20, 2006. Both applications are incorporated herein in their entirety.

The present invention relates to protein variants of CTLA-4, which show increased activity compared to wild-type in a cell assay and which exhibit increased stability. Such variants, are useful for treatment of disorders whereby attenuation of the T cell response would be beneficial.

The regulation of T-cell activity is dependent upon antigen-specific and co-stimulatory signals. One of the most important T cell co-stimulatory signals is mediated through the CD28-CD80/86 pathway. CD28 is present on most T cells and binds CD80 (B7-1) and CD86 (B7-2), present on antigen presenting cells (APC). Engagement of CD28 and B7 molecules provides a signal for T cell activation. Cytotoxic T lymphocyte-associated antigen (CTLA) 4 (CD152) is up regulated on activated T cells and also interacts with the B7 molecules interrupting the CD28 activating pathway and providing a negative signal that attenuates the T cell response.

CTLA-4 is homologous to CD28 and its gene maps to the same chromosomal band as the gene for CD28. CTLA-4 was identified by differential screening of a murine cytolytic T cell cDNA library (Brunet et al., (1987) Nature 328:267-270). Human CTLA-4 was first cloned by Dariavach et al (Eur J. Immunol. (1988) 18(12):1901-5). Expression was first reported using a soluble genetic fusion of the extracellular domain to an Fc domain and this fusion protein was shown to be a potent inhibitor of in vitro immune responses dependent upon cellular interactions between T and B lymphocytes (Linsley et al., J. Exp. Med. (1991) 174:561-569). The structure of CTLA-4 extra cellular domain is characteristic of the immunoglobulin variable domain. The human CTLA-4 precursor sequence is identified by the Swiss-Prot primary accession number: P16410. CTLA-4 appears to be critical for the negative regulation of T cell responses (Waterhouse et al., (1995) Science 270:985). Blockade of CTLA-4 has been found to remove inhibitory signals, while aggregation of CTLA-4 has been found to provide inhibitory signals that downregulate T cell responses (Allison and Krummel, (1995) Science 270:932). The B7 molecules have a higher affinity for CTLA-4 than for CD28 (Linsley et al., (1991) J. Exp. Med. 174: 561-569) and B7-1 and B7-2 have been found to bind to distinct regions of the CTLA-4 molecule and have different kinetics of binding to CTLA-4 (Linsley et al., (1994) Immunity 1:793).

The importance of the B7:CD28/CTLA-4 costimulatory pathway has been demonstrated in vitro and in several in vivo model systems. Blockade of this costimulatory pathway results in the development of antigen specific tolerance in murine and human systems (Harding et al., (1992) Nature 356:607-609; Lenschow et al., (1992) Science 257:789-792; Turka et al., (1992) Proc. Natl. Acad. Sci. USA 89:11102-11105; Gimmi et al., (1993) Proc. Natl. Acad. Sci. USA 90:6586-6590; Boussiotis et al., (1993) J. Exp. Med. 178: 1753-1763). Conversely, expression of B7 by B7 negative murine tumor cells induces T-cell mediated specific immunity accompanied by tumor rejection and long lasting protection to tumor challenge (Chen et al., (1992) Cell 71:1093-1102; Townsend and Allison, (1993) Science 259:368-370; Baskar et al., (1993) Proc. Natl. Acad. Sci. 90:5687-5690.). Therefore, manipulation of the costimulatory pathways offers great potential to stimulate or suppress immune responses in humans.

Activation of CTLA-4, for example, transmits a negative signal to a T cell. Engagement of CTLA-4 inhibits IL-2 production and can induce cell cycle arrest (Krummel and Allison, (1996) J. Exp. Med. 183:2533). In addition, mice that lack CTLA-4 develop lymphoproliferative disease (Tivol et al., (1995) Immunity 3: 541; Waterhouse et al., (1995) Science 270:985). The blockade of CTLA-4 with antibodies may remove an inhibitory signal, whereas aggregation of CTLA-4 with antibody transmits an inhibitory signal.

CTLA-4-Ig (abatacept, Orencia,) is the extracellular domain of CTLA-4 fused to the Fc of IgG1, the resulting soluble protein is a dimer with a molecular weight of approximately 92 kDa. It is being developed by Bristol-Myers Squibb Co (BMS) for rheumatoid arthritis (RA) and has the potential to treat various immunological disorders including RA, multiple sclerosis (MS) and systemic lupus erythematosus (SLE). Abatacept contains in its CDR3-like domain the amino acid hexapeptide motif MYPPPY, which is shared between CD28 and CTLA-4 and is necessary for binding to the B7 ligands. Mutation of the first tyrosine (Y) in this motif to alanine (A) abolishes binding to CD80, but also results in reduced binding to CD86, whereas a phenylalanine (F) substitution allows for retention of the full affinity for CD80 with a total loss of CD86 binding (Harris et al., J. Exp. Med. (1997) 185:177-182). Residues in the CDR3-like and CDR1-like regions are also important for the interaction of abatacept with its ligands. Thus, a mutant molecule with glutamic acid (E) instead of leucine (L) at position 104 and tyrosine (Y) instead of alanine (A) at position 29 exhibits approximately 2-fold greater binding avidity for CD80 (B7-1) and approximately 4-fold greater binding avidity for CD86 (B7-2) than abatacept. This compound LEA-29Y (belatacept) is being developed by BMS as an immunosuppressant for transplantation (Larsen et al., Am. J. Transplantation (2005) 5:443-453).

The leader sequence that is cleaved off CTLA-4 is not defined in the literature or public databases. Therefore, at least two different numbering systems are possible. The CTLA-4 sequence can start with, inter alia, Ala at position 1 (U.S. Pat. No. 5,434,131) or with Met at position 1 (Larsen et al., Am. J. Transplantation (2005) 5:443-453). For example the numbering referred to above relating to belatacept specifies Met at position 1. Unless context clearly dictates otherwise, the numbering system used herein is that wherein position 1 is Ala and position 2 is Met.

A further CTLA-4 product exists in the form of a CTLA-4 immunoglobulin fusion protein (U.S. Pat. No. 6,750,334; Repligen Corporation). This CTLA-4-Cγ4 product is a genetically engineered fusion protein that is comprised of natural CTLA-4 fused to a portion of an immunoglobulin to make a soluble form of CTLA-4. The immunoglobulin constant region, comprising a hinge region and CH2 and CH3 domains, is modified by substitution, addition or deletion of at least one amino acid residue, to reduce complement activation or Fc receptor interaction.

| Variant | Hillslope | IC50 |
| --- | --- | --- |
| 1A-D6 (SEQ ID No: 1) | −0.4830 | 5.622e−010 |
| 1A-C6 (SEQ ID No: 2) | −0.4806 | 1.111e−009 |
| 1A-B6 (SEQ ID No: 3) | −0.5684 | 1.366e−009 |
| 1A-A6 (SEQ ID No: 4) | −0.3807 | 1.203e−009 |
| WT (SEQ ID No: 8) | −1.142 | 1.273e−008 |

Figure 2:
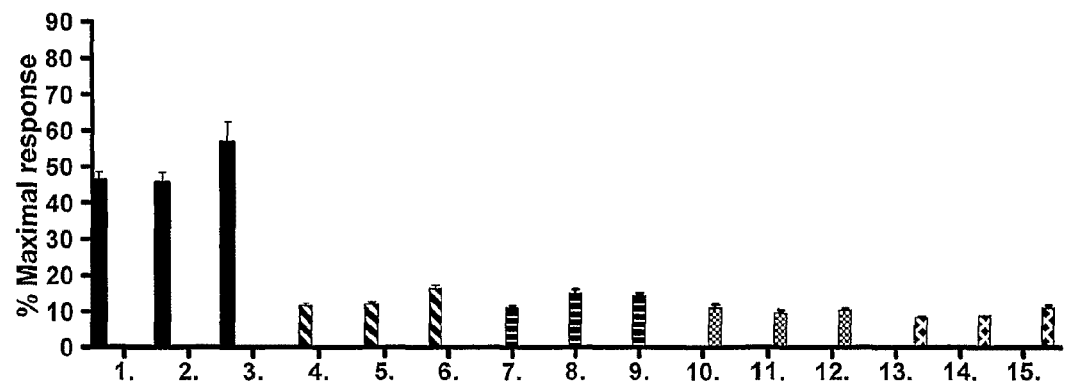

FIG. 2 shows the relative potency of WT and variants in an assay measuring B7-1 interactions, by blocking B7-2 with an anti B7-2 antibody, allowing only interaction between the WT and variants and the B7-1 receptor. Bars 1-3 show WT CTLA-4 at 2 nM, 1 nM and 0.5 nM, respectively. Bars 4-6 show the variant A06 at 2 nM, 1 nM and 0.5 nM, respectively. Bars 7-9 show the variant B06 at 2 nM, 1 nM and 0.5 nM, respectively. Bars 10-12 show the variant C06 at 2 nM, 1 nM and 0.5 nM, respectively. Bars 13-15 show the variant D06 at 2 nM, 1 nM and 0.5 nM, respectively.

FIG. 3 shows the relative potency of WT and variants in an assay measuring B7-2 interactions, by blocking B7-1 with an anti B7-1 antibody, allowing only interaction between the WT and variants and the B7-2 receptor. Bars 1-3 show WT CTLA-4 at 2 nM, 1 nM and 0.5 nM, respectively. Bars 4-6 show the variant A06 at 2 nM, 1 nM and 0.5 nM, respectively. Bars 7-9 show the variant B06 at 2 nM, 1 nM and 0.5 nM, respectively. Bars 10-12 show the variant C06 at 2 nM, 1 nM and 0.5 nM, respectively. Bars 13-15 show the variant D06 at 2 nM, 1 nM and 0.5 nM, respectively.

FIG. 4 shows the homology model of CTLA-4 variant DOG interacting with B7-1. The cartoon of B7-1 is in mid grey with the residue Arg 97 highlighted as mid grey sphere. The ribbon of CTLA-4 and the variant are shown in light grey. Mutated residues in the variant D06 are highlighted as black spheres (Pro26, Leu 71 and Glu 94) and dark grey spheres (Ser 17, Ser28, Ser 59) and labelled in bold text. One residue from CTLA-4 (Lys 94) is shown as a light grey sphere.

FIG. 5 shows alignment of IMGT IgSF numbering for the amino acid sequence of CTLA-4 variant D06 and V-like-domain antibody, vernier residues. Mutations in CTLA-4 are highlighted in black box with white letters. Vernier residues are highlighted in black box with white V.

The present invention provides variants of CTLA-4 with increased potency and/or stability and methods for producing such molecules. These variants provide increased efficacy for therapeutic treatment and formulation of CTLA-4 derived products. For example more potent CTLA-4 variants would reduce the efficacious dose. More stable CTLA-4 variants would allow formulation for subcutaneous dosing rather than iv infusion, thus improving patient convenience.

By utilising appropriately designed selection techniques and cell assays, we have developed CTLA-4 protein variants that show increased potency or stability compared with wild-type CTLA-4. Furthermore, modelling of a CTLA-4 variant interacting with B7-1 molecule permitted identification of key residue positions influencing potency.

Preferred CTLA-4 variants in accordance with the present invention comprise a set of mutations as identified herein. The numbering system for the positions identified herein is that system which, when applied to human wild-type CTLA-4 sequence, results in position 1 being Ala, position 2 being Met, and so on as shown in SEQ ID NO: 8. By reference to the human wild-type CTLA-4 sequence this numbering system can be applied to other CTLA-4 polypeptides including CTLA-4 variants of the invention and known CTLA-4 variants such as belatacept.

Accordingly, in a first aspect the invention provides a CTLA-4 variant having a mutation at two or more of the following positions in the amino acid sequence of human wild-type CTLA-4 (SEQ ID NO: 8): 17, 26, 28, 29, 43, 46, 49, 54, 59, 61, 62, 66, 70, 71, 81, 86 and 94, said CTLA-4 variant having improved potency and/or improved stability compared with a CTLA-4 polypeptide having, at said positions, the amino acid of the human wild-type CTLA-4 (SEQ ID NO: 8), wherein said improved potency is at least a 2-fold reduction in $IC_{50}$ in an assay of IL-2 production using T-cells activated by B-cells, and wherein said improved stability is at least 10% residual binding calculated as the binding signal to B7-1 or B7-2 in the presence of 10 mM DTT divided by the binding signal to B7-1 or B7-2 in the absence of DTT, multiplied by 100.

As described in more detail below, certain CTLA-4 variants according to the invention have been shown to bind to B7-1 and B7-2 with high potency in an assay measuring T cell activation. CTLA-4 variants block the ligands B7-1 and B7-2 thereby preventing the additional activation signals from B7-1 and B7-2 and leading to reduced IL-2 production.

Drug potency is a measure of drug activity expressed in terms of the amount required to produce an effect. Typically a titration of a variant is compared in a cell assay and the $IC_{50}$ values reported. In functional assays, $IC_{50}$ is the concentration of a binding member that reduces a biological response by 500 of its maximum. $IC_{50}$ may be calculated by plotting % of maximal biological response as a function of the log of the binding member concentration, and using a software program such as Prism (GraphPad) to fit a sigmoidal function to the data to generate $IC_{50}$ values. The lower the $IC_{50}$ value, the more potent the drug.

CTLA-4 variants can be described as having increased potency as less is needed compared with a CTLA-4 polypeptide having, at said positions, the amino acid of the human wild-type CTLA-4 (SEQ ID NO: 8) to produce inhibition of the IL-2 production. This is also reflected in the reported $IC_{50}$ values. Preferred CTLA-4 variants have increased potency compared with human wild-type CTLA-4 (SEQ ID NO: 8).

Binding of a CTLA-4 variant may for example be measured via the production of IL-2, since the binding of CTLA-4 to B7-1 and B7-2 attenuates IL-2 production. Suitable assays may comprise detecting the amount of IL-2 produced, for example by ELISA.

A reduction in the amount of IL-2 production may be partial or total. In specific embodiments, CTLA-4 variants are provided that reduce IL-2 production by at least 50%, 75% or 80%, more preferably at least 85%, 90% or 95%, at the concentrations tested. Potency of the CTLA-4 variants may be determined or measured using one or more assays known to the skilled person and/or as described or referred to herein.

A CTLA-4 variant of the present invention having improved potency may have at least a 2-fold reduction, preferably at least a 5-fold reduction, more preferably at least a 10-fold reduction and most preferably at least a 20-fold reduction in $IC_{50}$ in an assay of IL-2 production using T-cells activated by B-cells as compared with a CTLA-4 polypeptide having, at said positions, the amino acid of the human wild-type CTLA-4 (SEQ ID NO: 8). A suitable assay is described further herein.

Stability can generally be defined as the propensity of the molecule to remain in its folded and active state. Naturally occurring molecules are usually of limited stability as their metabolism, and often their fast metabolism, is a key characteristic of their intrinsic mechanism of action in the body.

Usually, a stable protein in its folded and native structure cannot be degraded by proteases or other mechanisms. It is due to two key off pathways from the stable state by which proteins are usually eliminated in the body. These two are unfolding and aggregation. They are usually linked. Unfolding is the pathway of reverting the folded active molecule into a less folded state. Aggregation is the result of misfolding such that the molecule irreversibly turns into a non-active state. Both unfolding and aggregation significantly increase the protein's susceptibility to proteolytic or other digestion. In the present invention we have modified the folding and unfolding pathway of CTLA-4 such that the resulting entity is more stable.

According to a further aspect of the present invention there is provided a CTLA-4 variant with improved stability compared with a CTLA-4 polypeptide having, at said positions, the amino acid of the human wild-type CTLA-4 (SEQ ID NO: 8). Preferred CTLA-4 variants have increased stability compared with human wild-type CTLA-4 (SEQ ID NO: 8).

A measure of stability employed in the context of the present invention can be expressed as a ratio of ability of a CTLA-4 variant to bind to B7-1 or B7-2 in the presence of dithiothreitol (DTT), e.g. 10 mM DTT, as determined in a radioimmunoassay (RIA), and ability of the CTLA-4 variant to bind to B7-1 or B7-2 in the absence of DTT in the same radioimmunoassay. A comparison of the relative binding of a CTLA-4 variant to B7-1 in the absence and presence of DTT provides an indication of stability. When binding is measured as a percentage value, the greater the percentage value, the greater the stability of the CTLA-4 variant.

Compared with a CTLA-4 polypeptide having, at said positions, the amino acid of the human wild-type CTLA-4 (SEQ ID NO: 8), a CTLA-4 variant of the invention may have such a percentage value of at least about 10%, 20%, 30% or 40%, more preferably, of at least about 50%, 60%, 70%, 75% or 80%. Preferably, a CTLA-4 variant of the invention has such a percentage value compared with human wild-type CTLA-4 (SEQ ID NO: 8).

Variants with improved stability are identified in the experiments described below. See for instance Table 1, which provides a percentage value determined by B7-1 binding in the presence and absence of DTT for wild-type CTLA-4 (0%) and three variants (ranging from 11% to 75%).

Variants with improved stability generally provide for a higher expression and higher yield in downstream processing which results in improved cost of goods. Further, CTLA-4 variants with improved stability have an improved shelf life. Longer shelf life is beneficial as it also influences the cost of goods.

A CTLA-4 variant with improved stability may have increased efficacy in the body, resulting from a longer half life. Further, a CTLA-4 variant with improved stability may be more amenable to routes of administration such as subcutaneous administration, because of reduced aggregation, which not only increases efficacy but also reduces the risk of neutralising or binding antibodies being elicited.

A CTLA-4 variant according to the present invention may contain one or more additional changes compared with a parent CTLA-4 polypeptide. The parent may be wild-type or natural protein, or a mutant or variant that contains one, or more differences in amino acid sequence from the wild-type. A number of different mutants and variants of CTLA-4 proteins are known (both naturally occurring mutants and artificially created variants) with modified properties compared with wild-type. One or more of these properties may be retained or provided in a CTLA-4 variant according to the present invention. A preferred CTLA-4 variant which may be further varied in accordance with the invention is belatacept (Larsen et al., Am. J. Transplantation (2005) 5:443-453). For example, a CTLA-4 variant according to the invention may comprise a variant of belatacept having a mutation at one or more of said positions. The sequence of belatacept is given below as SEQ ID NO: 9.

Preferred variants provided by the present invention include any wherein the residue provided at any one of said positions is selected from those identified in the following table:

| Position | Amino acid residue |
|----------|-------------------|
| 17 | S, V, T |
| 26 | P |
| 28 | S |
| 29 | N |
| 43 | G |
| 46 | S |
| 49 | W, Y |
| 54 | V |
| 59 | S |
| 61 | S |
| 62 | P |
| 66 | T |
| 70 | I |
| 71 | F, L |
| 81 | R |
| 86 | V, T |
| 94 | E |

Preferred variants provided by the present invention include any wherein the residue provided at position 26 is other than Y and/or wherein the residue provided at position 28 is other than L and/or wherein the residue provided at position 29 is other than F. Thus, preferred variants according to the invention may have other than the mutations S26Y, G28L and/or K29F. Preferred variants provided by the present invention include any wherein the residues provided at any of positions 17, 26, 28, 29, 43, 46, 49, 54, 59, 61, 62, 66, 70, 71, 81, 86 and/or 94 are other than the corresponding residues from CD28.

A CTLA-4 variant of the invention may comprise a sequence with ten or fewer, preferably five, six, seven or eight substitutions relative to a parent CTLA-4 polypeptide. The parent CTLA-4 polypeptide may be human wild-type CTLA-4 having the amino acid sequence SEQ ID NO:8 or a mutant or variant thereof, such as belatacept. The parent CTLA-4 polypeptide may be a mutant or variant of the human wild-type CTLA-4 which mutant or variant has, at each of positions 17, 26, 28, 29, 43, 46, 49, 54, 59, 61, 62, 66, 70, 71, 81, 86 and 94, the amino acid of the human wild-type CTLA-4 (SEQ ID NO: 8).

Thus, a CTLA-4 variant of the invention may have a discrete number of substitutions relative to the parent CTLA-4 polypeptide and thereby have improved potency and/or stability compared with the parent CTLA-4 polypeptide, such as human wild-type CTLA-4 or belatacept.

More preferably the CTLA-4 variant of the invention comprises substitutions selected from the group consisting of the following sets of mutations:

| | Substitution |
|---|---|
| (i) | I17S, S26P, G28S, L59S, S71L, K94E |
| (ii) | S26P, M54V, L59S, S71F, K94E |
| (iii) | I17V, S26P, K29N, L59S, I66T, S71F, M86V, K94E |
| (iv) | S26P, L59S, T70I, S71F, M86T, K94E |
| (v) | I17T, S26P, C49Y, L59S, F61S, S71F, K94E |

| Substitution | |
|---|---|
| (vi) | S26P, S43G, T46S, L59S, S71F, Q81R, K94E |
| (vii) | S26P, C49W, L59S, L62P, S71F, Q81R, K94E |

Further preferred CTLA-4 variants in accordance with the present invention have an amino acid sequence selected from SEQ ID NOs: 1, 2, 3, 4, 5, 6 and 7.

A CTLA-4 variant of the invention having said improved potency may have a mutation at one or more of the following positions in the amino acid sequence of human wild-type CTLA-4 (SEQ ID NO: 8): 17, 26, 28, 29, 54, 59, 66, 70, 71, 86 and 94.

Preferably, a CTLA-4 variant having said improved potency has the residue provided at any one of positions 17, 26, 28, 29, 54, 59, 66, 70, 71, 86 and 94 selected from those identified in the following table:

| Position | Amino acid residue |
|---|---|
| 17 | S, V |
| 26 | P |
| 28 | S |
| 29 | N |
| 54 | V |
| 59 | S |
| 66 | T |
| 70 | I |
| 71 | F, L |
| 86 | V, T |
| 94 | E |

CTLA-4 variants in which residue 26 was P, residue 59 was S, residue 71 was F or L and residue 94 was E, tended to exhibit greater potency for both B7-1 and B7-2 relative to human wild-type CTLA-4 having the amino acid sequence SEQ ID NO: 8. Thus preferably a CTLA-4 protein variant of the invention comprises an amino acid sequence in which residue 26 is P, residue 59 is S, residue 71 is F or L and residue 94 is E.

Further preferred CTLA-4 variants showing improved potency in accordance with the present invention have an amino acid sequence selected from SEQ ID NOs: 1, 2, 3 and 4.

A CTLA-4 variant of the invention having said improved stability may have a mutation at one or more of the following positions in the amino acid sequence of human wild-type CTLA-4 (SEQ ID NO: 8): 17, 26, 43, 46, 49, 59, 61, 62, 71, 81 and 94.

Preferably, a CTLA-4 variant having said improved stability has the residue provided at any one positions 17, 26, 43, 46, 49, 59, 61, 62, 71, 81 and 94 selected from those identified in the following table:

| Position | Amino acid residue |
|---|---|
| 17 | T |
| 26 | P |
| 43 | G |
| 46 | S |
| 49 | W, Y |
| 59 | S |
| 61 | S |
| 62 | P |
| 71 | F |
| 81 | R |
| 94 | E |

CTLA-4 variants in which residue 26 was P, residue 59 was S, residue 71 was F and residue 94 was E, tended to exhibit greater stability as further described herein. Thus preferably a CTLA-4 protein variant of the invention comprises an amino acid sequence in which residue 26 is P, residue 59 is S, residue 71 is F and residue 94 is E.

Further preferred CTLA-4 variants showing improved stability in accordance with the present invention have an amino acid sequence selected from SEQ ID NOs: 5, 6 and 7.

Preferred CTLA-4 variants may have one or more (such as one, two, three, four, five, ten or more) mutations at a position or positions which influence the structure and/or orientation of one or more CDR loops of CTLA-4. Such mutations may include an amino acid substitutions.

Mutation at a position which influences the structure and/or orientation of one or more CDR loops of CTLA-4 is thought to alter the binding interaction between CTLA-4 and B7 molecules thereby altering, in particular improving, the potency of CTLA-4 variants compared with human wild-type CTLA-4. Particularly preferred are variants wherein the mutation at a position which influences the structure and/or orientation of one or more CDR loops of CTLA-4 is one which improves potency, at least in part, by a mechanism selected from: alteration of the CDR3 loop to improve the fit with B7 molecules; removal of energetically unfavourable side chains; and increase of the overall charge complementarity between CTLA-4 and a B7 molecule.

A position which influences the structure and/or orientation of one or more CDR loops may be a position identified as a vernier position. Vernier positions and methods for identifying vernier positions in CTLA-4 are further described herein.

Preferred CTLA-4 variants have two or more amino acid substitutions compared with wild-type human CTLA-4 at a vernier position or positions shown in FIG. 5. As can be seen by reference to the alignment of FIG. 5, vernier residues are predicted at the following positions of the human wild-type amino acid sequence of CTLA-4 (SEQ ID NO: 8); the corresponding position number according to the IMGT IgSF numbering system being shown in brackets: 3(3), 17(18), 26(28), 27(29), 28(30), 29(31), 47(52), 48(53), 49(54), 67(76), 69(78), 71(80), 76(87), 94(105), 95(106), 106(118). Preferred CTLA-4 variants have one or more amino acid substitutions at a vernier position or positions selected from the following: 26(28), 28(30), 71(80) and 94(105). As explained further in Example 5 below, these four vernier positions were also mutated positions in CTLA-4 variants having improved potency compared with human wild-type CTLA-4. Particularly preferred CTLA-4 variants have one or more amino acid substitutions selected from the group consisting of: S26P, G28S, S71L and K94E.

A variant having a mutation at a position which influences the structure and/or orientation of one or more CDR loops of CTLA-4 additionally comprises one or more additional mutations, including any mutation described herein.

Each of the sets of mutations disclosed herein may be included within a CTLA-4 variant that has a set of mutations consisting of the identified sets of mutations. Each of these sets of mutations may be included within a CTLA-4 variant comprising the identified set of mutations and one or more additional mutations, especially one or more mutations disclosed herein as preferred mutations.

A polypeptide according to the present invention may be isolated and/or purified (e.g. using an antibody) for instance after production by expression from encoding nucleic acid (for which see below). Thus, a polypeptide may be provided free or substantially free from contaminants. A polypeptide may be provided free or substantially free of other polypeptides. The isolated and/or purified polypeptide may be used in formulation of a composition, which may include at least one additional component, for example a pharmaceutical composition including a pharmaceutically acceptable excipient, vehicle or carrier. A composition including a polypeptide according to the invention may be used in prophylactic and/or therapeutic treatment as discussed below.

A convenient way of producing a polypeptide according to the present invention is to express nucleic acid encoding it, by use of the nucleic acid in an expression system. Accordingly, the present invention also encompasses a method of making a polypeptide (as disclosed), the method including expression from nucleic acid encoding the polypeptide (generally nucleic acid according to the invention). This may conveniently be achieved by growing a host cell in culture, containing such a vector, under appropriate conditions which cause or allow expression of the polypeptide. Polypeptides may also be expressed in in vitro systems, such as reticulocyte lysate.

Systems for cloning and expression of a polypeptide in a variety of different host cells are well known. Suitable host cells include bacteria, eukaryotic cells such as mammalian and yeast, and baculovirus systems. Mammalian cell lines available in the art for expression of a heterologous polypeptide include Chinese hamster ovary cells, HeLa cells, baby hamster kidney cells, COS cells and many others. A common, preferred bacterial host is *E. coli*. Suitable vectors can be chosen or constructed, containing appropriate regulatory sequences, including promoter sequences, terminator fragments, polyadenylation sequences, enhancer sequences, marker genes and other sequences as appropriate. Vectors may be plasmids, viral e.g. 'phage, or phagemid, as appropriate. For further details see, for example, Molecular Cloning: a Laboratory Manual: 3rd edition, Sambrook and Russell, 2001, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Ausubel et al. eds., John Wiley & Sons, 1992.

Nucleic acid encoding a polypeptide of the invention is provided as a further aspect of the invention.

Generally, nucleic acid according to the present invention is provided as an isolate, in isolated and/or purified form, or free or substantially free of contaminants. Nucleic acid may be wholly or partially synthetic and may include genomic DNA, cDNA or RNA.

Nucleic acid may be provided as part of a replicable vector, and also provided by the present invention are a vector including nucleic acid encoding a CTLA-4 variant of the invention, particularly any expression vector from which the encoded polypeptide can be expressed under appropriate conditions, and a host cell containing any such vector or nucleic acid. An expression vector in this context is a nucleic acid molecule including nucleic acid encoding a polypeptide of interest and appropriate regulatory sequences for expression of the polypeptide, in an in vitro expression system, e.g. reticulocyte lysate, or in vivo, e.g. in eukaryotic cells such as COS or CHO cells or in prokaryotic cells such as *E. coli*.

A further aspect of the present invention provides a host cell containing nucleic acid as disclosed herein. The nucleic acid of the invention may be integrated into the genome (e.g. chromosome) of the host cell. Integration may be promoted by inclusion of sequences which promote recombination with the genome, in accordance with standard techniques. The nucleic acid may be on an extra-chromosomal vector within the cell.

A still further aspect provides a method which includes introducing the nucleic acid into a host cell. The introduction, which may (particularly for in vitro introduction) be generally referred to without limitation as "transformation" or "transfection", may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage.

Marker genes such as antibiotic resistance or sensitivity genes may be used in identifying clones containing nucleic acid of interest, as is well known in the art.

The introduction may be followed by causing or allowing expression from the nucleic acid, e.g. by culturing host cells (which may include cells actually transformed although more likely the cells will be descendants of the transformed cells) under conditions for expression of the gene, so that the encoded polypeptide is produced. If the polypeptide is expressed coupled to an appropriate signal leader peptide it may be secreted from the cell into the culture medium. Following production by expression, a polypeptide may be isolated and/or purified from the host cell and/or culture medium, as the case may be, and subsequently used as desired, e.g. in the formulation of a composition which may include one or more additional components, such as a pharmaceutical composition which includes one or more pharmaceutically acceptable excipients, vehicles or carriers (e.g. see below).

Each and every one of the variants disclosed herein represents an aspect of the invention, as do encoding nucleic acid, a vector comprising such nucleic acid, a host cell comprising such a vector, a composition comprising a variant, a variant of the invention for use in a method of treatment of the human or animal body, use of a variant in the manufacture of a medicament for treatment of rheumatoid arthritis, multiple sclerosis and/or systemic lupus erythematosus, a method of making the variant and other compositions, methods and uses as disclosed herein.

Furthermore, a CTLA-4 variant according to the present invention containing two or more additional changes compared with the parent protein, or compared with the wild-type or natural protein, may show increased potency or stability attributable to the synergistic combination of the one or more mutations.

Following production of a CTLA-4 variant by expression, its activity, for example its ability to bind to B7-1 or B7-2 can be tested routinely.

According to a further aspect of the present invention there is provided a method of making a CTLA-4 variant with improved potency and/or stability compared with a parent CTLA-4 polypeptide, the method comprising:
producing the CTLA-4 variant by expression from encoding nucleic acid, the CTLA-4 variant having a mutation compared with the parent CTLA-4 polypeptide at two or more of the following positions in the amino acid sequence of human wild-type CTLA-4 (SEQ ID NO: 8): 17, 26, 28, 29, 43, 46, 49, 54, 59, 61, 62, 66, 70, 71, 81, 86 and 94; and testing the CTLA-4 variant for improved potency and/or stability compared with said parent CTLA-4 polypeptide.

The CTLA-4 variant may contain a set of mutations as disclosed herein with one or more additional mutations. Such additional mutations may comprise conservative substitution. By "conservative substitution" is meant substitution of a first amino acid residue with a second, different amino acid residue, wherein the first and second amino acid residues have side chains which have similar biophysical characteristics.

Similar biophysical characteristics include hydrophobicity, charge, polarity or capability of providing or accepting hydrogen bonds. Examples of conservative substitutions include changing serine to threonine or tryptophan, glutamine to asparagine, lysine to arginine, alanine to valine, aspartate to glutamate, valine to isoleucine, asparagine to serine.

Such a method may optionally include isolating and/or purifying the CTLA-4 variant following its production and prior to testing.

Someone performing the method may additionally perform a prior step of providing a CTLA-4 variant by altering the amino acid sequence of the parent or starting CTLA-4 polypeptide, e.g. by substitution and/or insertion of one or more amino acids as discussed. Various different CTLA-4 variants may be provided and tested for the desired activity, e.g. in order to identify from a range of CTLA-4 variants one or more CTLA-4 variants with the properties desired in accordance with the present invention. Normally, alteration of the amino acid sequence of CTLA-4 will be made by altering the coding sequence of nucleic acid encoding CTLA-4. One or more nucleotides may be altered to alter one or more codons and thus the encoded amino acid(s). As mentioned elsewhere herein, and will be apparent to those skilled in the art, any suitable technique for mutagenesis, especially directed or site-specific mutagenesis, can be employed in order to change the coding sequence, and thus the encoded amino acid sequence, for a CTLA-4 polypeptide.

A further aspect of the present invention provides a method of identifying or obtaining a CTLA-4 variant with improved potency and/or stability compared with a parent CTLA-4 polypeptide, the method comprising:

mutating nucleic acid encoding the parent CTLA-4 polypeptide to provide one or more nucleic acids with sequences encoding one or more CTLA-4 variants having altered amino acid sequences at two or more of the following positions in the amino acid sequence of human wild-type CTLA-4 (SEQ ID NO: 8): 17, 26, 28, 29, 43, 46, 49, 54, 59, 61, 62, 66, 70, 71, 81, 86 and 94;

expressing the nucleic acid or nucleic acids to produce the CTLA-4 variant or variants;

testing the CTLA-4 variant or variants thus produced for improved potency and/or stability compared with said parent CTLA-4' polypeptide.

A library or diverse population of CTLA-4 variants may be produced and tested for the desired abilities.

The CTLA-4 polypeptide that is subject to the mutation may comprise any set of mutations disclosed herein and may have an amino acid sequence selected from SEQ ID NO: 1, 2, 3, 4, 5, 6 and 7. The CTLA-4 polypeptide that is subject to the mutation may have an amino acid sequence selected from SEQ ID NO: 8 and 9.

Selection from a library or diverse population may employ a display system such as phage display and/or ribosome display (for review, see Lowe D and Jermutus L, (2004) Curr. Pharm, Biotech, 517-27; WO92/01047). Selection for variants of improved stability may involve comparison of binding or, other indicator of activity when the variants are produced in the presence and absence of DTT, e.g. as disclosed herein.

One or more CTLA-4 variants with the desired properties may be identified or selected.

After a CTLA-4 variant of the invention has been identified or obtained it may be provided in isolated and/or purified form, it may be used as desired, and it may be formulated into a composition comprising at least one additional component, such as a pharmaceutically acceptable excipient or carrier. Nucleic acid encoding the CTLA-4 variant may be used to produce the variant for subsequent use. As noted, such nucleic acid may, for example, be isolated from a library or diverse population initially provided and from which the CTLA-4 variant was produced and identified.

According to a further aspect of the present invention there is provided a method of making a CTLA-4 variant with improved potency compared with a parent CTLA-4 polypeptide, the method comprising:

identifying two or more vernier positions which influence the structure and/or orientation of one or more CDR loops of said parent CTLA-4 polypeptide; and providing a mutation at two or more of said vernier positions, wherein said mutation enhances the ability of the CTLA-4 variant to bind a B7 molecule compared with said parent CTLA-4 polypeptide. Said vernier positions may preferably be selected from the following positions in the amino acid sequence of human wild-type CTLA-4 (SEQ ID NO: 8): 26, 28, 71 and 94. Said parent CTLA-4 polypeptide may be human wild-type CTLA-4 having the amino acid sequence of SEQ ID NO: 8 or a mutant or variant thereof. The parent CTLA-4 polypeptide may have the amino acid sequence of SEQ ID NO: 9.

A CTLA-4 variant in accordance with the present invention may be used in methods of diagnosis or treatment of the human or animal body of subjects, preferably human.

Accordingly, methods of treatment may comprise administration of a CTLA-4 variant as provided, pharmaceutical compositions comprising such a CTLA-4 variant, and use of such a CTLA-4 variant in the manufacture of a medicament for administration, for example in a method of making a medicament or pharmaceutical composition comprising formulating the CTLA-4 variant with a pharmaceutically acceptable excipient.

Clinical indications in which a CTLA-4 variant may be used to provide therapeutic benefit include autoimmune diseases such as rheumatoid arthritis, multiple sclerosis and systemic lupus erythematosus and transplantation.

A CTLA-4 variant may be given to an individual, preferably by administration in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors.

A composition may be administered alone or in combination with other treatments, either simultaneously or sequentially dependent upon the condition to be treated.

Pharmaceutical compositions according to the present invention, and for use in accordance with the present invention, may include, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be any suitable route, but most likely injection (with or without a needle), especially subcutaneous injection. Other preferred routes of administration include administration by inhalation or intranasal administration.

For intravenous, subcutaneous or intramuscular injection, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, or Lactated Ringer's Injection. Preservatives, stabilisers, buffers, antioxidants and/or other additives may be included, as required.

Further aspects and embodiments of the present invention will be apparent to those skilled in the art in the light of the present disclosure, including the following experimental exemplification.

All documents mentioned anywhere in this specification are incorporated by reference.

EXPERIMENTAL

Example 1

Construction of Library of CTLA-4 Variants and Selecting for Improved Potency

Library Construction

CTLA-4 cDNA was obtained from Invitrogen. To prevent dimerisation of the CTLA-4 the cysteine 121 in the dimerisation interface was mutated to a serine. The mature sequence was reformatted into the ribosome display linear template, which was subsequently used for library creation. At the DNA level, a T7 promoter was added at the 5'-end for efficient transcription to mRNA. At the mRNA level, the construct contained a prokaryotic ribosome-binding site (Shine-Dalgarno sequence). At the 3' end, a portion of gIII was added to act as a spacer (Hanes et al., Meth. Enzymol. (2000) 328: 404). A library of variants was created using error prone PCR, following the manufacturer's protocol (BD Bioscience), with an error rate of 8.1 nucleotide mutations/molecule. This introduced 4 mutations per molecule and a library of approximately $2.5 \times 10^{10}$ variant molecules.

Selection for Improved Potency

Ribosome display affinity based selections were performed using reducing concentrations of human B7-1 (RnD Systems, 140-B1) and/or B7-2 (RnD Systems, 141-B2) as described in Hanes et al. (supra). In brief, for each round of selection the library was incubated with the B7 molecules, the Fc fused B7 was coupled to protein G coated paramagnetic beads (Dynal M280)® and bound tertiary complexes (mRNA-ribosome-scFv) were recovered by magnetic separation whilst unbound complexes were washed away. The mRNA encoding the bound CTLA-4's were then rescued by RT-PCR as described in Hanes et al. (supra) and the selection process repeated with decreasing concentration (50 nM-10 pM over 5 rounds) of human B7 present during the selection.

The PCR products from the selections were cloned into the pEU7.1 vector for expression in HEK-293 cells. In brief the outputs were PCR amplified to introduce a 5' BssHII restriction site and at the 3' end a NotI restriction site. The product was gel purified, double digested with NotI and BssHII (New England Biolabs) and gel purified. The digested product was ligated into NotI BssHII digested pEU7.1 and transformed into E. coli DH5alpaha cells. Individual colonies were picked into 96 well plates for sequencing and preparation for expression.

Following the first phase of affinity selections, variants with 2-3 fold improved potency where identified. Five of these variants were used as template for a second random mutagenesis library, as described above. The library was selected in a second phase with decreasing concentration (5 nM-70 fM over 5 rounds) of human B7 and cloned as described above Example 2

Expression of CTLA-4 Variants

The variants were initially expressed in a medium throughput format for testing in a single cell assay. Hits from this were then expressed on a larger scale to provide material for confirmatory assays.

Medium Throughput Expression and Purification of CTLA-4 Variants.

Candidate CTLA-4 variants were expressed in parallel with parent wild-type and LEA29Y controls. Two days before transfection HEK-EBNA 293 cells were seeded in 12-well plates using D-MEM (Invitrogen, 41966) containing 10% FBS (Invitrogen, 10100-147) and 1% non-essential amino acids (Invitrogen, 11140-035) at a density of $2.5 \times 10^5$/well and grown in a humidified incubator, 37° C., 5% $CO_2$. Immediately prior to transfection spent culture medium was aspirated and replaced with 1 ml per well D-MEM containing 5% FBS. For each well to be transfected, 4 µg plasmid DNA was mixed with 5 µg Lipofectamine 2000 (Invitrogen, 11668-019) in D-MEM and incubated at room temperature for 45 min before adding to well. Plates were incubated in a humidified incubator, 37° C., 5% $CO_2$ overnight. The following morning, transfection medium was aspirated and replaced with 1.5 ml per well CD-CHO medium (Invitrogen, 10743-011) containing 8 mM L-Glutamine (Invitrogen, 25030-024), 2% HT supplement (Invitrogen, 41065-012), 1% Optimab A (Invitrogen, 11908-035) and 1% Optimab B (Invitrogen, 11909-033), then incubated in a humidified incubator, 37° C., 5% $CO_2$ for 5 days to allow for expression of protein into the growth medium. Following expression, spent culture medium containing protein was clarified by centrifugation at 1500×g for 5 min and stored at 4° C. until purification. Micro-scale protein purification was performed on a MiniTrak® liquid handling robot (Perkin Elmer) in a 96-well format, using PhyTip® Protein A affinity columns (Phynexus, PTP-92-20-01, 20 µl resin bed volume). Clarified crude supernatants were passed over the PhyTip® columns; which were then washed with 200 µl D-PBS, 200 µl 140 mM NaCl, eluted with 100 µl 100 mM HEPES pH 3.0, 140 mM NaCl and neutralised with 100 µl 200 mM HEPES pH 8.0, 140 mM NaCl.

Large-Scale Expression and Purification of CTLA-4 Variants

Candidate CTLA-4 variants were expressed in parallel with parent wild-type and LEA29Y controls. Two days before transfection HEK-EBNA 293-6E cells (obtained from Durocher et al.) were seeded in Freestyle 293 medium (Invitrogen, 12338-018) containing 0.99% Pluronic® (Invitrogen, 24040-032) and 0.05% Geneticin® (Invitrogen, 10131) at a density of $5 \times 10^5$/ml and grown in a humidified shaker incubator, 120 rpm, 37° C., 5% $CO_2$. Immediately prior to transfection cells were centrifuged at 1500×g, then resuspended in fresh Freestyle 293 medium containing 0.99% Pluronic® and 0.05%

Geneticin® to achieve a density of 1×10⁶/ml. For each CTLA-4 variant a 50 ml volume of these cells was transfected by mixing 50 μg plasmid DNA with 200 μg polyethylenimine (Polysciences Inc., linear 25 kDa, 9002-98-6) in Freestyle 293 medium, incubating for 1 h at room temperature and adding to a 250 ml flask containing 50 ml cells. Cultures were grown in a humidified shaker incubator, 120 rpm, 37° C., 5% $CO_2$ for 5 days to allow for expression of protein into the growth medium. Following expression, spent culture medium containing protein was clarified by centrifugation at 1500×g for 5 min and stored at 4° C. until purification. Purifications were performed using an ASPEC XL4 liquid handling robot (Gilson). Affinity columns were poured using 0.5 ml bed volumes of Protein A resin (Biosepra, Ceramic Hyper D F, 20078-28) and equilibrated with 50 mM Tris.Cl pH 8.0, 250 mM NaCl. Each 50 ml clarified crude supernatant sample was passed over a single Protein A column, washed with 15 ml 50 mM Tris.Cl pH 8.0, 250 mM NaCl, eluted in 1.15 ml 100 mM sodium citrate pH 3.0 and neutralised with 100 μl 2M Tris.Cl pH 10.0. Neutralised eluates were buffer-exchanged into 1.5 ml D-PBS (Invitrogen, 14190-094) using NAP-10 columns (GE Healthcare, 17-0854-01) that had been equilibrated with D-PBS.

Example 3

The Biological Activity of Variant and Wild-Type CTLA-4 was Assessed in a Jurkat (T-cell) and Raji (B-cell) Dual Cell Assay Co-culture of Jurkat and Raji cells in the presence of phytohemagglutinin (PHA), results in the production of IL-2. PHA activates the TCR on Jurkat cells and additional essential activation signals via CD28 are provided by B7-1 and B7-2 ligand on Raji cells. The IL-2 is then detected via ELISA. The production of IL-2 is attenuated by CTLA-4 binding to 137-1 and B7-2 on Raji cells. Jurkat cells were obtained from ECAC and Raji cells from ECCAC and maintained according to supplied protocols. Assay media comprised RPMI containing 10% v/v foetal bovine serum. Prior to each assay, Jurkat and Raji were pelleted by centrifugation at 300×g for 5 mins, the media removed by aspiration and the cells re-suspended in assay media at a final concentration of 2×10⁶/ml. CTLA-4 variants (in duplicate) were diluted to the desired concentrations in assay media. In this assay the CTLA-4 variants and CTLA-4 human wild-type had cysteine at position 121 because the variants and the wild-type were tested in the CTLA-4-Fc form. 50 111 of each of the re-suspended cells were then added to each assay point to give a total assay volume of 250 μl/well. Assay plates were incubated at 37° C. was for 24 hours at 37° C. under 5% $CO_2$. The resultant IL2 produced was then detected via a Duoset ELISA (R&D Systems Cat No DY202), which had been converted to a DELFIA® europium readout.

Figure 1:
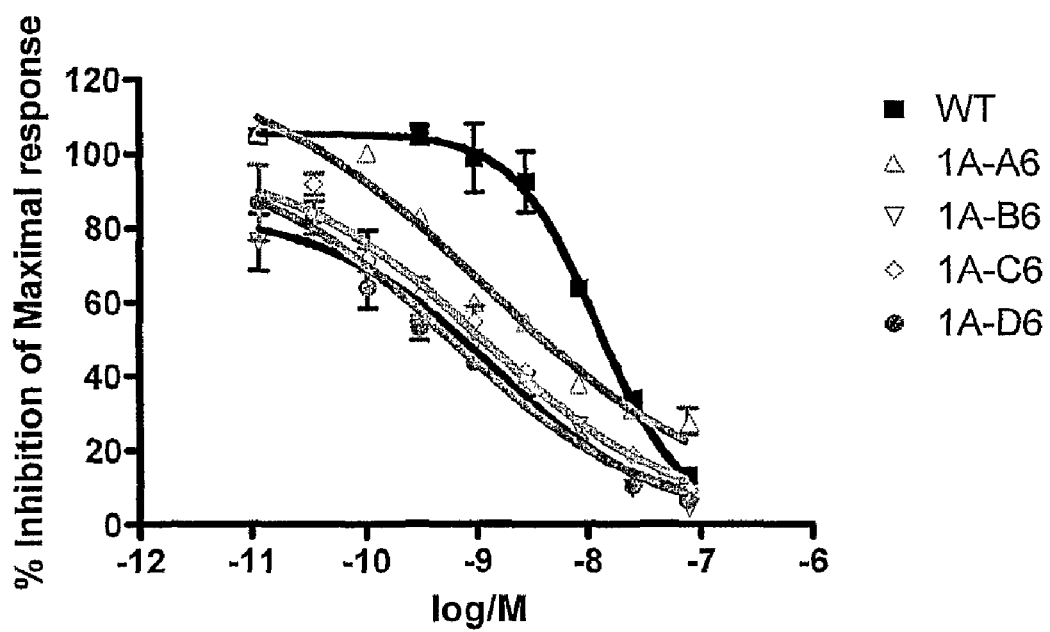
FIG. 1 shows the inhibition of IL-2 production by CTLA-4 wild-type (WT) and variants from Jurkat cells (100,000 cells/well) and Raji cells (100,000 cells/well).

Variants with 10-20 fold-improved potency in comparison to WT were identified (FIG. 1). This improved potency is likely due to an increase in affinity for B7-1 and B7-2 ligands. The sequence of four of the variants is recorded as SEQ ID 1, 2, 3 and 4.

Example 4

Assessment of Comparative Activity of WT and Variants for Each B7 Receptor

Raji cells express B7-1 and B7-2. To assess the effects of CTLA-4 variants against each B7 receptor, B7-1 or B7-2 were selectively blocked with specific antibodies. The relative activity of four variants and wild-type for the B7-1 and B7-2 receptors was assessed in a Jurkat (T-cell) and Raji (B-cell) cell assay by blocking the receptors with anti B7-2 and anti B7-1 antibodies respectively in the presence of PHA. Jurkat and Raji cells were maintained according to supplied protocols. Assay media comprised RPMI containing 10.0% v/v foetal bovine serum. Prior to each assay, Jurkat and Raji were pelleted by centrifugation at 300×g for 5 mins, the media removed by aspiration and the cells re-suspended in assay media at a final concentration of 2×10⁶/ml. CTLA-4 variants (in triplicate) were diluted to the desired concentrations in assay media. In this, assay the CTLA-4 variants and CTLA-4 human wild-type had cysteine at position 121 because the variants and the wild-type were tested in the CTLA-4-Fc form. 50 μl of each of the re-suspended cells were then added to each assay point, alongside either anti B7-1 (R&D Systems Cat No Mab 140) or anti B7-2 (R&D Systems Cat No Mab 141) at 5 nM, to give a total assay volume of 250 μl/well. Assay plates were incubated at 37° C. for 24 hours at 37° C. under 56 $CO_2$. The resultant IL2 produced was then detected via a Duoset ELISA (R&D Systems Cat No DY202), which had been converted to a DELFIA® europium readout.

Figure 3:
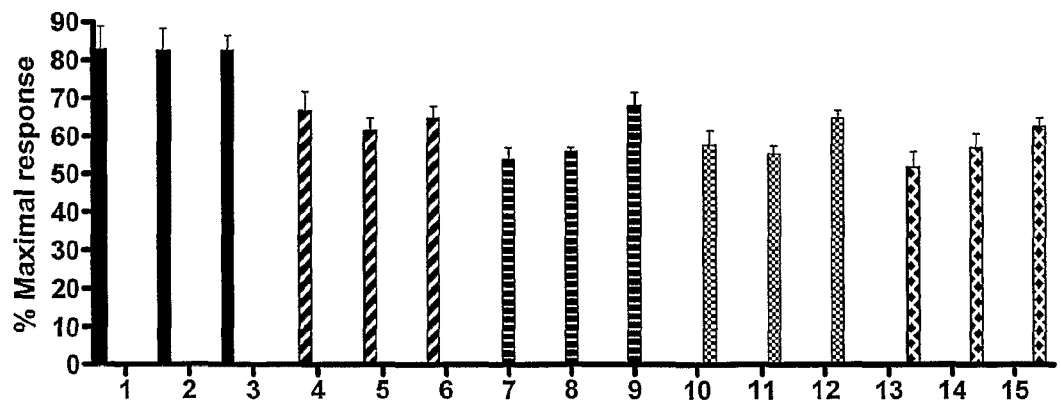
Figure 4:
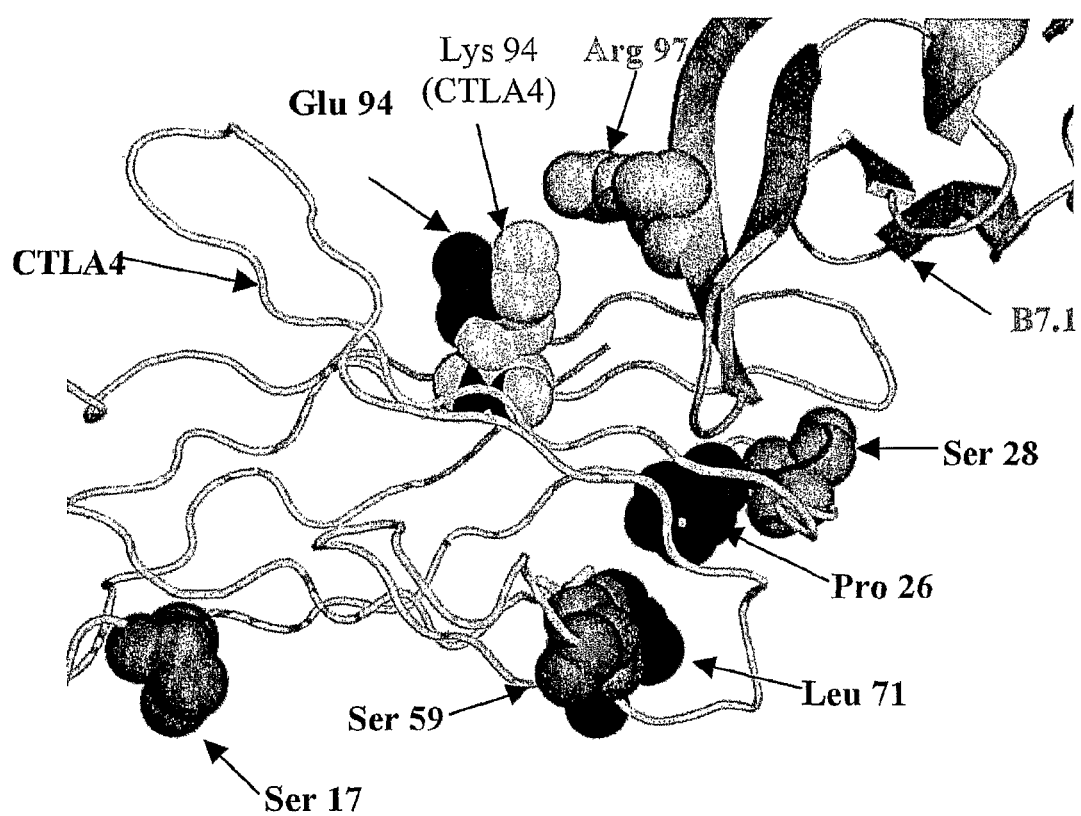

The four variants showed improved activity against B7-1 (FIG. 2) and B7-2 (FIG. 3) relative to wild-type. Comparing the potency of the variants for B7-1 and B7-2, the binding to B7-1 shows the greatest improvement.

Example 5

Modelling of CTLA-4 Variant Interacting with B7-1

The modelling of the CTLA-4 variant structure from the primary amino acid sequence was performed using Accelrys software DS Modeller 1.1 (REG™). Briefly, the software performed homology modelling by aligning the sequences of the variant CTLA-4 to the sequence of CTLA-4 in the x-ray crystal structure 1i8L of human CTLA-4 and B7.1 (Stamper et al 2001 Nature 410:608-611). Visualisation of the model was performed using PYMOL (DeLano 2002). The model is depicted in FIG. 4 which shows the interaction of CTLA-4 variant D06 (SEQ ID NO: 1) with B7-1.

Rationale for Improved Potency

Modelling D06 (SEQ ID NO: 1) shows there is little change in the position of residues in the CDR3 loop known to be important in binding B7-1 and B7-2. However, on examination of the mutations in the structural model and comparisons to other immunoglobulin V-like domains provides evidence that the beneficial mutations have a subtle mechanism of action.

The change at position 94 from positively charged Lys to negatively charged Glu is proximal to the B7-1 positively charged Arg. Without wishing to be bound by theory, it is believed that this change in charge could result in improved electrostatic interactions by removing the charge repulsion and introducing a salt bridge between D06 and B7-1.

The CTLA-4 structure is a V-like domain of the immunoglobulin superfamily (IgSF). A standard numbering scheme for IgSF V-like-domains has been proposed (Duprat et al 2004 Recent Res. Devel. Human Genet. 2:111-136). This includes CTLA-4 and other antibodies, which despite a large amino acid divergence in amino acid sequence share the same Ig structural fold. The fold consists of about 100 amino acids in antiparallel beta strands linked by beta turns or loops and stabilised in two layers by a disulphide bridge. Both antibodies and CTLA-4 have complementarity-determining region (CDR) loops that are responsible for the majority of the target binding interactions. Studies on antibodies have identified a set of residues that are able to fine-tune the fit of the CDRs to the target. These residues are known as the 'vernier' residues (Foote and Winter 1992 J. Mol. Biol. 224: 487-499). They exert their effect because in the 3D structure of the antibody variable region the vernier residues form a layer beneath the CDR loops and can influence the structure and orientation of the CDR loops. When CTLA-4 and the antibody vernier residues are aligned to the IgSF numbering scheme (FIG. 5), four of the mutations occur in vernier positions. The vernier residues are Pro 26, Ser 28, Leu 71 and Glu 94. Therefore, 4 out of the 6 mutations in D06 are in vernier positions. This significant finding was unexpected. Without wishing to be bound by theory, we believe that these beneficial mutations are not altering the principle side-chain contacts in CDR3, but may act via a more subtle approach. This could involve several mechanisms such as altering the CDR3 loop confirmation to improve fit with the B7 molecules, the removal of energetically unfavourable side chains or an increase in the overall charge complementarity. The possibility of CDR1 region altering CDR3 was noted by Peach et al 1994 (J Exp Med 180: 2049-2058). The residues Pro 26 and Ser 28 are in CDR1 and also vernier residues, thus supporting their role in altering the fit between CTLA-4 and B7.1. The mutation Ser 59, while not identified as homologous to a vernier residue, aligns to another set of antibody V-like-domain residues described as structural determining residues that are responsible for loop confirmation (Martin and Thornton 1996 J. Mol. Biol 263: 800-815). Ser 59 would alter the structure of CDR loop2.

Therefore, residues in positions which can influence the structure and orientation of the CDR loops of CTLA-4, in particular residues in vernier positions, will be expected to affect the potency of CTLA-4 variants.

Example 6

Selection of CTLA-4 Variants with Improved Stability

The second phase library described in Example 1 was selected for improved stability. The CTLA-4 variants and human wild-type had serine at position 121 so that they were in monomeric form. In vitro translations and selections were performed in the presence and absence of DTT as described in Jermutus et al., (2001). Following incubation of the stability selected library with B7-1 the fusion protein was captured and the bound complexes were recovered by magnetic separation whilst unbound complexes were washed away. The mRNA encoding the bound CTLA-4 variants was then recovered by RT-PCR and the selection process was repeated. Three rounds of selection were performed with increasing concentrations of DTT.

The PCR products from round 3 were cloned into the in vitro expression vector pIVEX2.3d (Roche). In brief the outputs were PCR amplified, with primers Nco1 reamp and Not1 reamp, to introduce a 5' Nco1 restriction site and at the 3' end a stop codon followed immediately by a Not1 restriction site. The stop codon allowed the expression of untagged variant CTLA-4. The product was gel purified, double digested with Not1 and Nco1 (New England Biolabs) and gel purified. The digested product was ligated into Not1 Nco1 digested pIVEX2.3d and transformed into *E. coli* TG1 cells. Individual colonies were picked into 96 well plates for screening and sequencing.

Example 7

Screening of Single CTLA-4 Variants in Primary Stability RIA

CTLA-4 variants were screened for stability using the primary stability RIA (radio immunoassay) as described in Jermutus et al., (2001). In brief for each variant a linear DNA template was amplified, transcribed, the mRNA purified on G25 Sephadex® columns and quantified. For each variant in vitro translations in the presence of $^{35}$S-labelled methionine were set up in duplicate at 30° C. for 30 min, one in non-reducing conditions and one in 10 mM DTT (dithiothreitol). The translations were stopped with PBS with 0.050 Tween 20, with DTT at the same concentration as the translations. The translation mixture was incubated on a plate coated with B7-1 for 1 hour at room temperature. Plates were washed three times in PBS with 0.05% Tween 20® and three times in PBS. The remaining radioactivity was eluted with 0.1 M triethylamine and quantified by liquid scintillation counting. A measure of the variants' stability was calculated as the percentage residual binding i.e. binding signal in presence of DTT, divided by binding signal in absence of DTT, multiplied by 100. The more stable the variants the larger the percentage residual binding.

Four variants were tested and from this three CTLA-4 variants were identified that were more stable than WT (Table 1).

TABLE 1

Results of stability RIA for WT AND three variants with RIA signal after non-reducing conditions (DTT-) given as signal over background and measure of stability calculated as percentage residual binding, described in the text.

| Clone | Signal DTT- | % Residual Binding |
|---|---|---|
| WT (SEQ ID 8) | 1.6 | 0 |
| Var 1 (SEQ ID 5) | 2.6 | 55 |
| Var 2 (SEQ ID 6) | 29.8 | 11 |
| Var 3 (SEQ ID 7) | 13.2 | 75 |

Sequence Analysis of CTLA-4 Variants

The CTLA-4 variants from round 3 were sequenced. The sequence of the three more stable variants is described below as SEQ ID NO 5, 6 and 7.

The invention claimed is:

1. A CTLA-4 polypeptide variant having improved potency or stability compared to the CTLA-4 polypeptide of SEQ ID NO: 8 comprising 4 to 10 amino acid substitutions compared to the CTLA-4 polypeptide of SEQ ID NO: 8 wherein 4 to 10 of the amino acid substitutions are selected from the following table:

| Position | Amino acid residue |
|---|---|
| 17 | S, V, T |
| 26 | P |
| 28 | S |
| 29 | N |
| 43 | G |
| 46 | S |
| 49 | W, Y |
| 54 | V |
| 59 | S |
| 61 | S |
| 62 | P |
| 66 | T |
| 70 | I |
| 71 | F, L |
| 81 | R |
| 86 | V, T |
| 94 | E | wherein said 4 to 10 amino acid substitutions include those at amino acid positions 26, 59, 71, and 94, wherein said improved potency is at least a 2-fold reduction in $IC_{50}$ in an assay of IL-2 production using T-cells activated by B-cells, and wherein said improved stability is at least 10% residual binding calculated as the binding signal to B7-1 or B7-2 in the presence of 10 mM DTT divided by the binding signal to B7-1 or B7-2 in the absence of DTT, multiplied by 100.

2. The CTLA-4 polypeptide variant according to claim 1, wherein the amino acid substitutions comprise a set of mutations selected from:

(i) I17S, S26P, G28S, L59S, S71L, K94E;

(ii) S26P, M54V, L59S, S71F, K94E;

(iii) I17V, S26P, K29N, L59S, I66T, S71F, M86V, K94E;

(iv) S26P, L59S, T70I, S71F, M86T, K94E;

(v) S26P, C49W, L59S, L62P, S71F, Q81R, K94E;

(vi) I17T, S26P, C49Y, L59S, F61S, S71F, K94E; and (vii) S26P, S43G, T46S, L59S, S71F, Q81R, K94E.

3. The CTLA-4 polypeptide variant according to claim 2, comprising an amino acid sequence selected from the group consisting of SEQ ID NOS: 1, 2, 3, 4, 7, 5, and 6.

4. A composition comprising a CTLA-4 polypeptide variant according to claim 1 and a pharmaceutically acceptable excipient.

5. A fusion protein comprising at least the extracellular domain of a CTLA-4 polypeptide variant according to claim 1 fused to a further polypeptide.

6. A fusion protein according to claim 5, wherein said further polypeptide comprises an immunoglobulin portion.

7. A method of treating rheumatoid arthritis in an individual, comprising administering to the individual a CTLA-4 variant according to claim 6.

8. The CTLA-4 polypeptide variant according to claim 1 wherein the T-cells are Jurkat T cells and the B-cells are Raji B-cells.

9. The CTLA-4 polypeptide variant according to claim 1 which is further mutated by substituting Tyr for Ala at amino acid position 30 and substituting Glu for Leu at amino acid position 105.

10. A CTLA-4 polypeptide variant having improved potency compared to the CTLA-4 polypeptide of SEQ ID NO: 8 comprising 4 to 10 amino acid substitutions compared to the CTLA-4 polypeptide of SEQ ID NO: 8 wherein 4 to 10 of the amino acid substitutions are selected from the following table:

| Position | Amino acid residue |
|---|---|
| 17 | S, V |
| 26 | P |
| 28 | S |
| 29 | N |
| 54 | V |
| 59 | S |
| 66 | T |
| 70 | I |
| 71 | F, L |
| 86 | V, T |
| 94 | E | wherein said 4 to 10 amino acid substitutions include those at amino acid positions 26, 59, 71, and 94, and wherein said improved potency is at least a 2-fold reduction in $IC_{50}$ in an assay of IL-2 production using T-cells activated by B-cells.

11. The CTLA-4 polypeptide variant according to claim 10, wherein the amino acid substitutions comprise a set of mutations selected from:
(i) I17S, S26P, G28S, L59S, S71L, K94E;
(ii) S26P, M54V, L59S, S71F, K94E;
(iii) 117V, S26P, K29N, L59S, I66T, S71F, M86V, K94E; and
(iv) S26P, L59S, T70I, S71F, M86T, K94E.

12. The CTLA-4 polypeptide variant according to claim 11, comprising an amino acid sequence selected from the group consisting of SEQ ID NOS: 1, 2, 3, and 4.

13. A CTLA-4 polypeptide variant having improved stability compared to the CTLA-4 polypeptide of SEQ ID NO: 8 comprising 4 to 10 amino acid substitutions compared to the CTLA-4 polypeptide of SEQ ID NO: 8 wherein 4 to 10 of the amino acid substitutions are selected from the following table:

| Position | Amino acid residue |
|---|---|
| 17 | T |
| 26 | P |
| 43 | G |
| 46 | S |
| 49 | W, Y |
| 59 | S |
| 61 | S |
| 62 | P |
| 71 | F |
| 81 | R |
| 94 | E | wherein said 4 to 10 amino acid substitutions include those at amino acid positions 26, 59, 71, and 94, and wherein said improved stability is at least 10% residual binding calculated as the binding signal to B7-1 or B7-2 in the presence of 10 mM DTT divided by the binding signal to B7-1 or B7-2 in the absence of DTT, multiplied by 100.

14. The CTLA-4 polypeptide variant according to claim 13, wherein the amino acid substitutions comprise a set of mutations selected from:
(i) S26P, C49W, L59S, L62P, S71F, Q81R, K94E;
(ii) I17T, S26P, C49Y, L59S, F61S, S71F, K94E; and
(iii) S26P, S43G, T46S, L59S, S71F, Q81R, K94E.

15. The CTLA-4 polypeptide variant according to claim 14, comprising an amino acid sequence selected from the group consisting of SEQ ID NOs: 7, 5, and 6.

16. A method of making a CTLA-4 polypeptide variant having improved potency or stability compared to the CTLA-4 polypeptide of SEQ ID NO: 8 comprising:
making 5 or more amino acid substitutions to the human CTLA-4 of SEQ ID NO: 8, where the amino acid positions substituted are selected from positions 17, 26, 28, 29, 43, 46, 49, 54, 59, 61, 62, 66, 70, 71, 81, 86, and 94; and
testing the CTLA-4 variant for improved potency and/or stability, wherein said improved potency is at least a 2-fold reduction in $IC_{50}$ in an assay of IL-2 production using T-cells activated by B-cells, and wherein said improved stability is at least 10% residual binding calculated as the binding signal to B7-1 or B7-2 in the presence of 10 mM DTT divided by the binding signal to B7-1 or B7-2 in the absence of DTT, multiplied by 100.

17. A method of making a CTLA-4 polypeptide variant having improved potency or stability compared to the CTLA-4 polypeptide of SEQ ID NO: 9 comprising:
making 5 or more amino acid substitutions to the human CTLA-4 of SEQ ID NO: 9, where the amino acid positions substituted are selected from positions 17, 26, 28, 29, 43, 46, 49, 54, 59, 61, 62, 66, 70, 71, 81, 86, and 94; and
testing the CTLA-4 variant for improved potency and/or stability, wherein said improved potency is at least a 2-fold reduction in $IC_{50}$ in an assay of IL-2 production using T-cells activated by B-cells, and wherein said improved stability is at least 10% residual binding calculated as the binding signal to B7-1 or B7-2 in the presence of 10 mM DTT divided by the binding signal to B7-1 or B7-2 in the absence of DTT, multiplied by 100.

18. A method of identifying or obtaining a CTLA-4 variant with improved potency and/or stability compared with a parent CTLA-4 polypeptide, wherein said parent CTLA-4 polypeptide is selected from the group consisting of a human wild-type CTLA-4 having the amino acid sequence of SEQ ID NO: 8, a CTLA-4 variant having the amino acid sequence of SEQ ID NO: 9, and a CTLA-4 variant with one amino acid difference compared to SEQ ID NO: 8, the method comprising:
mutating nucleic acid encoding the parent CTLA-4 polypeptide to provide one or more nucleic acids with sequences encoding one or more CTLA-4 variants having altered amino acid sequences at five or more of the following positions in the amino acid sequence of said parent CTLA-4 polypeptide: 17, 26, 28, 29, 43, 46, 49, 54, 59, 61, 62, 66, 70, 71, 81, 86 and 94;
expressing the nucleic acid or nucleic acids to produce the CTLA-4 variant or variants;
testing the CTLA-4 variant or variants thus produced for improved potency and/or stability compared with said parent CTLA-4 polypeptide, wherein said improved potency is at least a 2-fold reduction in $IC_{50}$ in an assay of IL-2 production using T-cells activated by B-cells, and wherein said improved stability is at least 10% residual binding calculated as the binding signal to B7-1 or B7-2 in the presence of 10 mM DTT divided by the binding signal to B7-1 or B7-2 in the absence of DTT, multiplied by 100 and wherein, optionally, a library or diverse population of CTLA-4 variants with altered amino acid sequences is produced and tested.

19. A method of making a CTLA-4 variant with improved potency compared with a parent CTLA-4 polypeptide, wherein said parent CTLA-4 polypeptide is human wild-type CTLA-4 having the amino acid sequence of SEQ ID NO: 8, the method comprising:
providing a mutation at two or more vernier positions selected from 26, 28, 71, and 94 in the amino acid sequence of SEQ ID NO: 8, wherein said mutation enhances the ability of the CTLA-4 variant to bind a B7 molecule compared with said parent CTLA-4 polypeptide.

* * * * *

UNITED STATES PATENT AND TRADEMARK OFFICE
CERTIFICATE OF CORRECTION

PATENT NO.        : 8,088,736 B2
APPLICATION NO.   : 12/446216
DATED             : January 3, 2012
INVENTOR(S)       : Franks et al.

It is certified that error appears in the above-identified patent and that said Letters Patent is hereby corrected as shown below:

In the Specification:

Column 1, lines 15-16, "variants, are" should read --variants are--.

Column 3, line 32, "DOG" should read --D06--.

Column 4, line 27, "500" should read --50%--.

Column 11, line 59, "CTLA-4'" should read --CTLA-4--.

Column 12, line 6, "or, other" should read --or other--.

Column 14, line 13, "above" should read --above.--.

Column 15, line 37, "137-1" should read --B7-1--.

Column 15, line 48, "50111 of" should read --50µl of--.

Column 16, line 21, "56" should read --5%--.

Column 16, line 36, "(REG™)." should read --(REG TM).--.

Column 18, line 25, "0.050" should read --0.05%--.

In the Claims:

Column 27, line 39, "117V" should read --I17V--.

Column 27, line 39, "166T" should read --I66T--.

Signed and Sealed this
Seventeenth Day of July, 2012

David J. Kappos
*Director of the United States Patent and Trademark Office*

SEQUENCE LISTING

<160> NUMBER OF SEQ ID NOS: 9

<210> SEQ ID NO 1
<211> LENGTH: 125
<212> TYPE: PRT
<213> ORGANISM: Homo sapiens -continued

<400> SEQUENCE: 1

Ala Met His Val Ala Gln Pro Ala Val Val Leu Ala Ser Ser Arg Gly
1               5                   10                  15

Ser Ala Ser Phe Val Cys Glu Tyr Ala Pro Pro Ser Lys Ala Thr Glu
            20                  25                  30

Val Arg Val Thr Val Leu Arg Gln Ala Asp Ser Gln Val Thr Glu Val
        35                  40                  45

Cys Ala Ala Thr Tyr Met Met Gly Asn Glu Ser Thr Phe Leu Asp Asp
    50                  55                  60

Ser Ile Cys Thr Gly Thr Leu Ser Gly Asn Gln Val Asn Leu Thr Ile
65                  70                  75                  80

Gln Gly Leu Arg Ala Met Asp Thr Gly Leu Tyr Ile Cys Glu Val Glu
                85                  90                  95

Leu Met Tyr Pro Pro Pro Tyr Leu Gly Ile Gly Asn Gly Thr Gln
                100                 105                 110

Ile Tyr Val Ile Asp Pro Glu Pro Cys Pro Asp Ser Asp
            115                 120                 125

<210> SEQ ID NO 2
<211> LENGTH: 125
<212> TYPE: PRT
<213> ORGANISM: Homo sapiens

<400> SEQUENCE: 2

Ala Met His Val Ala Gln Pro Ala Val Val Leu Ala Ser Ser Arg Gly
1               5                   10                  15

Ile Ala Ser Phe Val Cys Glu Tyr Ala Pro Pro Gly Lys Ala Thr Glu
            20                  25                  30

Val Arg Val Thr Val Leu Arg Gln Ala Asp Ser Gln Val Thr Glu Val
        35                  40                  45

Cys Ala Ala Thr Tyr Val Met Gly Asn Glu Ser Thr Phe Leu Asp Asp
    50                  55                  60

Ser Ile Cys Thr Gly Thr Phe Ser Gly Asn Gln Val Asn Leu Thr Ile
65                  70                  75                  80

Gln Gly Leu Arg Ala Met Asp Thr Gly Leu Tyr Ile Cys Glu Val Glu
                85                  90                  95

Leu Met Tyr Pro Pro Pro Tyr Leu Gly Ile Gly Asn Gly Thr Gln
                100                 105                 110

Ile Tyr Val Ile Asp Pro Glu Pro Cys Pro Asp Ser Asp
            115                 120                 125

<210> SEQ ID NO 3
<211> LENGTH: 125
<212> TYPE: PRT
<213> ORGANISM: Homo sapiens

<400> SEQUENCE: 3

Ala Met His Val Ala Gln Pro Ala Val Val Leu Ala Ser Ser Arg Gly
1               5                   10                  15

Val Ala Ser Phe Val Cys Glu Tyr Ala Pro Pro Gly Asn Ala Thr Glu
            20                  25                  30

Val Arg Val Thr Val Leu Arg Gln Ala Asp Ser Gln Val Thr Glu Val
        35                  40                  45

Cys Ala Ala Thr Tyr Met Met Gly Asn Glu Ser Thr Phe Leu Asp Asp
    50                  55                  60

Ser Thr Cys Thr Gly Thr Phe Ser Gly Asn Gln Val Asn Leu Thr Ile
65                  70                  75                  80

```
Gln Gly Leu Arg Ala Val Asp Thr Gly Leu Tyr Ile Cys Glu Val Glu
                85                  90                  95

Leu Met Tyr Pro Pro Pro Tyr Leu Gly Ile Gly Asn Gly Thr Gln
            100                 105                 110

Ile Tyr Val Ile Asp Pro Glu Pro Cys Pro Asp Ser Asp
        115                 120                 125

<210> SEQ ID NO 4
<211> LENGTH: 125
<212> TYPE: PRT
<213> ORGANISM: Homo sapiens

<400> SEQUENCE: 4

Ala Met His Val Ala Gln Pro Ala Val Val Leu Ala Ser Ser Arg Gly
1               5                   10                  15

Ile Ala Ser Phe Val Cys Glu Tyr Ala Pro Pro Gly Lys Ala Thr Glu
            20                  25                  30

Val Arg Val Thr Val Leu Arg Gln Ala Asp Ser Gln Val Thr Glu Val
        35                  40                  45

Cys Ala Ala Thr Tyr Met Met Gly Asn Glu Ser Thr Phe Leu Asp Asp
    50                  55                  60

Ser Ile Cys Thr Gly Ile Phe Ser Gly Asn Gln Val Asn Leu Thr Ile
65                  70                  75                  80

Gln Gly Leu Arg Ala Thr Asp Thr Gly Leu Tyr Ile Cys Glu Val Glu
                85                  90                  95

Leu Met Tyr Pro Pro Pro Tyr Leu Gly Ile Gly Asn Gly Thr Gln
            100                 105                 110

Ile Tyr Val Ile Asp Pro Glu Pro Cys Pro Asp Ser Asp
        115                 120                 125

<210> SEQ ID NO 5
<211> LENGTH: 125
<212> TYPE: PRT
<213> ORGANISM: Homo sapiens

<400> SEQUENCE: 5

Ala Met His Val Ala Gln Pro Ala Val Val Leu Ala Ser Ser Arg Gly
1               5                   10                  15

Thr Ala Ser Phe Val Cys Glu Tyr Ala Pro Pro Gly Lys Ala Thr Glu
            20                  25                  30

Val Arg Val Thr Val Leu Arg Gln Ala Asp Ser Gln Val Thr Glu Val
        35                  40                  45

Tyr Ala Ala Thr Tyr Met Met Gly Asn Glu Ser Thr Ser Leu Asp Asp
    50                  55                  60

Ser Ile Cys Thr Gly Thr Phe Ser Gly Asn Gln Val Asn Leu Thr Ile
65                  70                  75                  80

Gln Gly Leu Arg Ala Met Asp Thr Gly Leu Tyr Ile Cys Glu Val Glu
                85                  90                  95

Leu Met Tyr Pro Pro Pro Tyr Leu Gly Ile Gly Asn Gly Thr Gln
            100                 105                 110

Ile Tyr Val Ile Asp Pro Glu Pro Cys Pro Asp Ser Asp
        115                 120                 125

<210> SEQ ID NO 6
<211> LENGTH: 125
<212> TYPE: PRT
<213> ORGANISM: Homo sapiens
```

-continued

```
<400> SEQUENCE: 6

Ala Met His Val Ala Gln Pro Ala Val Val Leu Ala Ser Ser Arg Gly
1               5                   10                  15

Ile Ala Ser Phe Val Cys Glu Tyr Ala Pro Pro Gly Lys Ala Thr Glu
            20                  25                  30

Val Arg Val Thr Val Leu Arg Gln Ala Asp Gly Gln Val Ser Glu Val
        35                  40                  45

Cys Ala Ala Thr Tyr Met Met Gly Asn Glu Ser Thr Phe Leu Asp Asp
    50                  55                  60

Ser Ile Cys Thr Gly Thr Phe Ser Gly Asn Gln Val Asn Leu Thr Ile
65                  70                  75                  80

Arg Gly Leu Arg Ala Met Asp Thr Gly Leu Tyr Ile Cys Glu Val Glu
                85                  90                  95

Leu Met Tyr Pro Pro Pro Tyr Leu Gly Ile Gly Asn Gly Thr Gln
                100                 105                 110

Ile Tyr Val Ile Asp Pro Glu Pro Cys Pro Asp Ser Asp
            115                 120                 125

<210> SEQ ID NO 7
<211> LENGTH: 125
<212> TYPE: PRT
<213> ORGANISM: Homo sapiens

<400> SEQUENCE: 7

Ala Met His Val Ala Gln Pro Ala Val Val Leu Ala Ser Ser Arg Gly
1               5                   10                  15

Ile Ala Ser Phe Val Cys Glu Tyr Ala Pro Pro Gly Lys Ala Thr Glu
            20                  25                  30

Val Arg Val Thr Val Leu Arg Gln Ala Asp Ser Gln Val Thr Glu Val
        35                  40                  45

Trp Ala Ala Thr Tyr Met Met Gly Asn Glu Ser Thr Phe Pro Asp Asp
    50                  55                  60

Ser Ile Cys Thr Gly Thr Phe Ser Gly Asn Gln Val Asn Leu Thr Ile
65                  70                  75                  80

Arg Gly Leu Arg Ala Met Asp Thr Gly Leu Tyr Ile Cys Glu Val Glu
                85                  90                  95

Leu Met Tyr Pro Pro Pro Tyr Leu Gly Ile Gly Asn Gly Thr Gln
                100                 105                 110

Ile Tyr Val Ile Asp Pro Glu Pro Cys Pro Asp Ser Asp
            115                 120                 125

<210> SEQ ID NO 8
<211> LENGTH: 125
<212> TYPE: PRT
<213> ORGANISM: Homo sapiens

<400> SEQUENCE: 8

Ala Met His Val Ala Gln Pro Ala Val Val Leu Ala Ser Ser Arg Gly
1               5                   10                  15

Ile Ala Ser Phe Val Cys Glu Tyr Ala Ser Pro Gly Lys Ala Thr Glu
            20                  25                  30

Val Arg Val Thr Val Leu Arg Gln Ala Asp Ser Gln Val Thr Glu Val
        35                  40                  45

Cys Ala Ala Thr Tyr Met Met Gly Asn Glu Leu Thr Phe Leu Asp Asp
    50                  55                  60

Ser Ile Cys Thr Gly Thr Ser Ser Gly Asn Gln Val Asn Leu Thr Ile
65                  70                  75                  80
```

-continued

```
Gln Gly Leu Arg Ala Met Asp Thr Gly Leu Tyr Ile Cys Lys Val Glu
                85                  90                  95

Leu Met Tyr Pro Pro Pro Tyr Tyr Leu Gly Ile Gly Asn Gly Thr Gln
            100                 105                 110

Ile Tyr Val Ile Asp Pro Glu Pro Cys Pro Asp Ser Asp
        115                 120                 125

<210> SEQ ID NO 9
<211> LENGTH: 125
<212> TYPE: PRT
<213> ORGANISM: Homo sapiens

<400> SEQUENCE: 9

Ala Met His Val Ala Gln Pro Ala Val Val Leu Ala Ser Ser Arg Gly
1               5                   10                  15
Ile Ala Ser Phe Val Cys Glu Tyr Ala Ser Pro Gly Lys Tyr Thr Glu
            20                  25                  30

Val Arg Val Thr Val Leu Arg Gln Ala Asp Ser Gln Val Thr Glu Val
        35                  40                  45

Cys Ala Ala Thr Tyr Met Met Gly Asn Glu Leu Thr Phe Leu Asp Asp
    50                  55                  60
Ser Ile Cys Thr Gly Thr Ser Ser Gly Asn Gln Val Asn Leu Thr Ile
65                  70                  75                  80
Gln Gly Leu Arg Ala Met Asp Thr Gly Leu Tyr Ile Cys Lys Val Glu
                85                  90                  95

Leu Met Tyr Pro Pro Pro Tyr Tyr Glu Gly Ile Gly Asn Gly Thr Gln
            100                 105                 110

Ile Tyr Val Ile Asp Pro Glu Pro Cys Pro Asp Ser Asp
        115                 120                 125
```